United States Patent [19]

Smith et al.

[11] 3,945,973

[45] Mar. 23, 1976

[54] N,N'-DIGLYCIDYL-N,N'-DIALKYL ARYL DISULFONAMIDES

[75] Inventors: Harry A. Smith; Edward G. Bozzi, Jr., both of Midland, Mich.

[73] Assignee: The Dow Chemical Company, Midland, Mich.

[22] Filed: May 3, 1974

[21] Appl. No.: 466,595

[52] U.S. Cl. ............... 260/49; 260/2 EP; 260/2 EC; 260/79; 260/79.3 M; 260/329.3; 260/346.2 M; 260/348 R
[51] Int. Cl.² ............................................ C08G 75/30
[58] Field of Search .......... 260/47 EP, 49, 2 EP, 79, 260/79.3 M, 2 EC, 329.3, 346.2 M, 348 R

[56] References Cited
UNITED STATES PATENTS

| | | | |
|---|---|---|---|
| 2,643,244 | 6/1953 | Simons | 260/47 X |
| 2,671,771 | 3/1954 | Kenson | 260/47 |
| 3,014,895 | 12/1961 | Reynolds | 260/348.6 X |

*Primary Examiner*—Lester L. Lee
*Attorney, Agent, or Firm*—Benjamin G. Colley

[57] ABSTRACT

N,N'-diglycidyl-N,N'-dialkyl aryl disulfonamides are prepared having an epoxy equivalent weight range from about 234 to about 1100. These polyepoxides are useful to make coated articles having superior solvent resistance and impact resistance when cured with conventional epoxy curing agents.

3 Claims, No Drawings

N,N'-DIGLYCIDYL-N,N'-DIALKYL ARYL DISULFONAMIDES

BACKGROUND OF THE INVENTION

This invention relates to a N,N'-diglycidyl-N,N'-dialkyl aryl disulfonamide, a thermosettable composition comprising the polyepoxides and thermoset compositions comprising the polyepoxides.

It is known from U.S. Pat. No. 2,671,771 that epichlorohydrin and disulfonamides can be reacted to produce a thermosetting resin having very little epoxy groups if they are reacted at a 3:1 maximum molar ratio i.e. three moles of epi to one mole of disulfonamide in the presence of a strong base.

It is known from Ser. No. 363,204, filed May 23, 1973, that epichlorohydrin can be condensed with di-primary sulfonamides to produce polyepoxides. However, these polyepoxides, when cured, tend to be stiff, brittle, and unsuitable for coatings.

SUMMARY OF THE INVENTION

The products of this invention are represented by the formulae

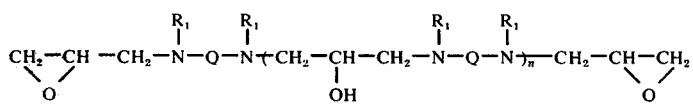

wherein $R_1$ is an alkyl group having 1–6 carbons; $R_2$ is independently hydrogen, an aliphatic hydrocarbon group having 1–6 carbons, chlorine, bromine or $-OR_3$ where $R_3$ is an acyl group having 1–6 carbons; $n$ is a whole number in the range 0–5.

The process of this invention comprises reacting a mole of a disecondary sulfonamide with 6 to 20 moles and preferably 10 to 20 moles of an epihalohydrin at a temperature in the range from about 70°C to the reflux temperature of the mixture and in the presence of a catalytic amount, preferably 0.5 to 5% by weight, of a quaternary ammonium salt until the reaction is complete and generally from 1 to 4 hours.

The resulting mixture is heated with a stoichiometric excess of a basic inorganic material such as an alkali metal hydroxide, carbonate or oxide or an alkaline earth metal hydroxide, carbonate, or oxide at a temperature in the range from 70°C to the reflux temperature for 1 to 2 hours and the polyepoxide is recovered by isolation of the organic layer, 2 water washings, and removal of excess epichlorohydrin from the polyepoxide by distillation.

The monomeric polyepoxides having an E.E.W. from about 234 to about 275 are then reacted with 2 to 5 moles of dimethyl diphenyloxide disulfonamide along with 0.1 to 1.0% of a tertiary amine or a phosphonium salt type catalyst at about 150°C for 1–3 hours. The reaction can be run in the presence of air, under $N_2$, or under vacuum to produce an epoxy resin polymer having an E.E.W. of about 600 to about 1100 and preferably from about 700 to about 900.

The polyepoxides of this invention can be mixed with conventional epoxy hardeners and cured on metal substrates to produce films having superior solvent resistance and superior adhesion as shown by reverse impact tests.

DETAILED DESCRIPTION

Suitable disulfonamides which are employed to produce the novel polyepoxides of the present invention include those represented by the general formulae:

wherein Q is a divalent aromatic disulfonyl group selected from

I. 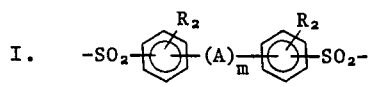

where A is a divalent hydrocarbon group having from 1 to 6 carbon atoms,

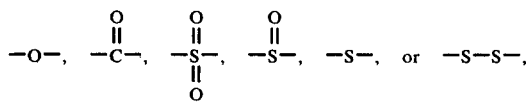

$m$ is 0 or 1

II. 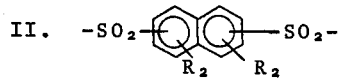

III. 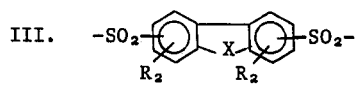

where X is oxygen or sulfur and

IV. 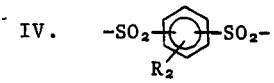

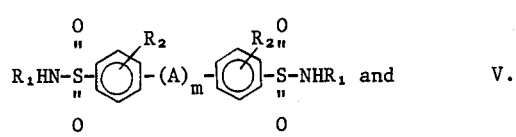 V.

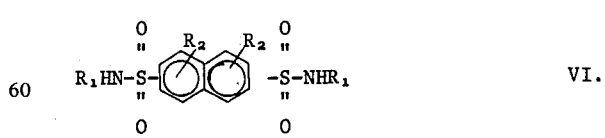 VI.

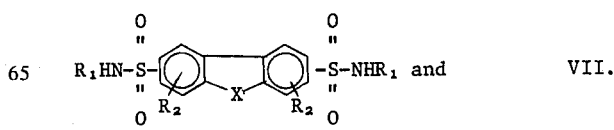 VII.

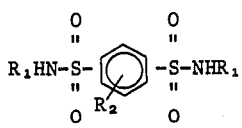

VIII.

wherein A, $R_1$, $R_2$, X and m are the same as above.

N,N'-Dialkyl disulfonamides such as represented by the above formulae V through VIII include, for example, N,N'-dimethyl-diphenylether-4,4'-disulfonamide; N,N'-dimethyldi(bromophenyl) ether-4,4'-disulfonamide; N,N'-dimethyldi(methylphenyl)ether-4,4'-disulfonamide; N,N'-dimethyl di(butylphenyl)ether-4,4'-disulfonamide; N,N'-dimethyldi(propylphenyl)ether-4,4'-disulfonamide; N,N'-dimethyldi(chlorophenyl)ether-4,4'-disulfonamide; N,N'-dimethylnaphthalene-1,5-disulfonamide; N,N'-dimethyl-methylnaphthalene-1,5-disulfonamide; N,N'-dimethyldipropylnaphthalene-1,5-disulfonamide; N,N'-dimethyl-chloronaphthalene-1,5-disulfonamide; N,N'-dimethyl-bromonaphthalene-1,5-disulfonamide; N,N'-dimethyl-dibromonaphthalene-1,5-disulfonamide; N,N'-dimethylmeta- and para-phenylene disulfonamides; N,N'-dimethyl dibenzofuran disulfonamide; N,N'-dimethyl dibenzothiophene disulfonamide; mixtures thereof, and the higher dialkyl derivatives such as N,N'-diethyl, propyl butyl, pentyl, and hexyl.

Suitable quaternary ammonium salt catalysts useful in this invention to prepare the monomeric polyepoxides are benzyl trimethylammonium sulfate, benzyl trimethylammonium nitrate, benzyl trimethylammonium thiocyanate, diphenyldimethyl ammonium chloride, diphenyldimethyl ammonium nitrate, benzyl trimethyl ammonium chloride and the like and mixtures thereof.

Suitable epihalohydrins which are employed in the process of the present invention include epichlorohydrin, epibromohydrin, epiiodohydrin, and mixtures thereof.

Suitable alkali and alkaline earth metal hydroxides include sodium hydroxide, potassium hydroxide, calcium hydroxide, barium hydroxide, mixtures thereof and the like.

Suitable alkali and alkaline earth metal carbonates include sodium carbonate, potassium carbonate, barium carbonate, calcium carbonate, magnesium carbonate, mixtures thereof and the like.

Suitable alkaline earth metal oxides include barium oxide, calcium oxide, magnesium oxide, mixtures thereof and the like.

The unreacted epihalohydrin is conveniently removed by any of the well known methods such as for example, flashing at elevated temperature and reduced pressure, extraction with liquid aliphatic hydrocarbons, e.g., pentane or hexane, combinations thereof and the like.

The polyepoxide product is conveniently recovered by any of the well known methods for recovery such as, for example, solvent extraction, with subsequent evaporation of the solvent, water washing, combinations thereof and the like.

Suitable catalysts for epoxy chain lengthening include any tertiary amines such as: 2-methyl-imidazole, benzyl dimethyl amine, triethylene, diamine, N-methyl morpholine. Phosphonium salts such as tetrabutyl phosphonium chloride, and tetrabutyl phosphonium acetate can also be used when air is present.

If desired, the chain extending reaction with N,N'-dimethyl diphenyl ether disulfonamide can be conducted in the presence of an inert polar high boiling solvent such as nitromethane, chlorobenzene ethylene glycol ethyl ether, ethylene glycol methyl ether, propylene glycol ethyl ether, propylene glycol methyl ether, and the like, In such cases, it is necessary to use ammonium catalysts such as benzyl trimethyl ammonium chloride, benzyl triethyl ammonium bromide, diphenyl dimethyl ammonium chloride, benzyl trimethyl ammonium sulfate, diphenyl dimethyl ammonium nitrate, and the like.

The N,N'-disubstituted sulfonamide starting materials are conveniently prepared by chlorosulfonating the desired aromatic compound with at least a stoichiometric quantity of a suitable chlorosulfonation agent such as, for example, chlorosulfonic acid at a temperature of from about 50°C to reflux for from about 2 to about 6 hours or longer. The resultant disulfonyl chloride after removal of any excess chlorosulfonation agent is then reacted with primary alkyl amines at reflux temperature for about 1 to about 24 hours. if desired, the disulfonyl chloride can be reacted with primary alkyl amines under autogeneous pressure at 100°C in less than one hour. The resultant N,N'-dialkyl sulfonamide which precipitates is filtered, and the product is finally recovered by slurrying the precipitate in hot water and again filtering.

The compositions of the present invention are believed to be mixtures of polyepoxides and in as much as the particular position of the sulfonamide groups or a substituent on the aromatic ring is not believed to be of any particular concern, no attempts have been made to determine such positions. What is important, is that the polyepoxides of the present invention have more than one epoxy group per molecule. However, the sulfonamide groups are usually in the 4,4'-positions when a diphenyl ether is employed and the 1,5-positions when a naphthalene is employed.

Suitable catalysts and curing agents which are employed to cure the polyepoxides of the present invention include the well known epoxy catalysts and curing agents such as primary, secondary and tertiary amines, polybasic acids and anhydrides, polyamides, Lewis acids, mixtures thereof and the like.

The type and quantity of catalyst and/or curing agent employed depends upon the physical properties desired of the cured product.

Inert fillers, fire retardant agents, accelerators, extenders, pigments and other modifiers may be added to the compositions of the present invention to modify the properties thereof.

The following examples are illustrative of the present invention and are not to be construed as to limiting the scope thereof in any manner.

EXAMPLE 1

A solution of 88.8 grams (0.25 mole) of N,N'-dimethyldiphenyl ether disulfonamide dissolved in 200 grams (2.2 moles) of epichlorohydrin was added dropwise over a two-hour period to a hot (105°C) solution of 260.6 grams (2.8 moles) of epichlorohydrin and 1.6 grams (0.005 mole) of benzyl trimethyl ammonium chloride. The reaction mixture was kept at 105°C for an additional hour after the addition was complete.

The next step was the dropwise addition of 52.8 grams of a 50% aqueous sodium hydroxide solution over a one-hour period with temperature of the reactants at 95°C. The reaction mixture was then cooled to 25°C, washed twice with water and the excess epichlorohydrin, removed by a vacuum distillation to give 125.0 grams of a viscous liquid polyepoxide. The polyepoxide had a epoxy equivalent weight of 265. The theoretical E.E.W. value for this polyepoxide is 234.

Example 1 was repeated twenty times yielding polyepoxide having E.E.W.'s ranging from 260–275.

EXAMPLE 2

In a reaction flask was placed 20.0 grams (0.044 mole) of the polyepoxide of Example 1, 5.4 grams (0.016 mole) of N,N'-dimethyl diphenylether disulfonamide, 0.20 grams of benzyl trimethyl ammonium chloride, and 40 grams of ethylene glycol methyl ether. This mixture was refluxed for 6½ hours at 115°C. After cooling the reaction flask, 200 cc of water was added to precipitate the resin. The mixture was filtered to yield 23.3 grams of an off-white solid resin having an E.E.W. of 425 and a softening point range from 65° to 67°C.

EXAMPLE 3

In a 500 cc reaction flask was placed 53.2 grams (0.2 equiv.) of a polyepoxide prepared by the procedure of Example 1 having a E.E.W. = 266, 17.8 grams (0.05 mole) of N,N'-dimethyl diphenylether disulfonamide, and 0.36 grams of 2-methyl imidazole. The system was purged with nitrogen for 10 minutes and then the mass was heated to 150°C in one hour under nitrogen. It was held at 150°C for 35 minutes and then cooled yielding 79.8 grams or 89.4% of a light tan solid softening and melting at 90°–110°C. The E.E.W. was 700 and the molecular weight 1470.

EXAMPLE 4

Example 3 was repeated several times allowing a small amount of air (about 10 cc) to be introduced into the reactor each time. This resulted in similar materials to Example 3 but having an E.E.W. range of 850–1150 and molecular weights range of 1450–1700 depending on the length of reaction (35–45 minutes at 150°C).

EXAMPLE 5

A mixture of 2.0 grams of the polyepoxide of Example 1 and 1.0 grams of D.E.H. 14 (a semisolid polyamide sold by the Dow Chemical Company having a viscosity of about 200–600 cps at 40°C) was allowed to stand at 25°C for 4 hours.

This mixture was then coated on a test panel of Bonderite 37 treated cold rolled steel to give a ½ mil coating. The coated panel was then cured for 20 minutes at 150°C in an oven. The cured coating showed no change after 10 minutes exposure to methyl ethyl ketone and the panel had a reverse impact resistance of about 160 in. lbs.

EXAMPLE 6

A mixture of 4.9 grams (0.007 equiv.) of the polyepoxide of Example 3, 0.57 grams (0.007 equiv.) of diphenylether disulfonamide, and 0.11 grams of 2-methylimidazole in 5.6 grams of ethyleneglycol monomethyl ether was made up and coated onto a 4 × 9 inch piece of Bonderite 37 treated steel panel. The coating was cured for 20 minutes at 175°C resulting in a cured coating which had a reverse impact resistance 160 inch pounds and was not effected by 10 minutes exposure to methyl ethyl ketone.

EXAMPLE 7

Example 6 was repeated with the resins of Example 4 with comparable results.

EXAMPLE 8

To 5.0 grams of the polyepoxide of Example 3 was added 0.63 grams of trimellitic anhydride, 0.06 grams of benzyl dimethylamine and 5.7 grams of ethyleneglycol monomethyl ether. The resulting solution was coated onto a 4 × 9 inch aluminum panel and cured 20 minutes at 175°C. The cured coating had a reverse impact resistance greater than the aluminum (50–60 inch pounds) and was not effected by exposure to methyl ethyl ketone.

We claim:

1. A polyepoxide represented by the formulae:

$$CH_2-CH-CH_2-N-Q-N\underset{\underset{R_1}{|}}{\overset{\overset{R_1}{|}}{}}(CH_2-CH-CH_2-N-Q-N\underset{\underset{R_1}{|}}{\overset{\overset{R_1}{|}}{}})_n-CH_2-CH-CH_2$$
$$\overset{\diagdown}{\phantom{x}}\underset{O}{\diagup}\phantom{xxxxxxxxxxxxx}\overset{|}{OH}\phantom{xxxxxxxxxxxx}\overset{\diagdown}{\phantom{x}}\underset{O}{\diagup}$$

wherein Q is a divalent aromatic disulfonyl group selected from

I. $-SO_2-\underset{}{\bigcirc}-(A)_m-\underset{}{\bigcirc}-SO_2-$ with $R_2$ substituents where A is a divalent hydrocarbon group having from 1 to 6 carbon atoms, $$-O-,\ -\overset{O}{\underset{}{\overset{||}{C}}}-,\ -\overset{O}{\underset{O}{\overset{||}{\underset{||}{S}}}}-,\ -\overset{O}{\underset{}{\overset{||}{S}}}-,\ -S-,\ or\ -S-S-,$$

$m$ is 0 or 1

II. $-SO_2-\underset{R_2}{\bigcirc}\underset{R_2}{\bigcirc}-SO_2-$

III. $-SO_2-\underset{R_2}{\bigcirc}-X-\underset{R_2}{\bigcirc}-SO_2-$ where X is oxygen or sulfur and IV. $-SO_2-\underset{R_2}{\bigcirc}-SO_2-$ wherein $R_1$ is an alkyl group having 1–6 carbons; $R_2$ is independently hydrogen, an aliphatic hydrocarbon group having 1–6 carbons, chlorine, bromine or $-OR_3$ where $R_3$ is an acyl group having 1–6 carbons; $n$ is a whole number in the range 0–5.

2. A polyepoxide as set forth in claim 1 wherein the polyepoxide has the formula I and has an epoxy equivalent weight range from about 234 to about 275.

3. A polyepoxide as set forth in claim 1 wherein the polyepoxide has the formula I and has an epoxy equivalent weight range from about 600 to about 1100.

* * * * *